United States Patent
Feingold et al.

(10) Patent No.: US 9,468,363 B2
(45) Date of Patent: Oct. 18, 2016

(54) POWER SUPPLY THROUGH A SINGLE TRACK OF DISCRETE ELECTRODES AND METHOD THEREFOR

(71) Applicants: Benjamin H. Feingold, Tucson, AZ (US); James C. Waring, San Francisco, CA (US); John T. Shen, San Jose, CA (US)

(72) Inventors: Benjamin H. Feingold, Tucson, AZ (US); James C. Waring, San Francisco, CA (US); John T. Shen, San Jose, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 344 days.

(21) Appl. No.: 14/195,962

(22) Filed: Mar. 4, 2014

(65) Prior Publication Data

US 2014/0275780 A1    Sep. 18, 2014

Related U.S. Application Data

(60) Provisional application No. 61/782,632, filed on Mar. 14, 2013.

(51) Int. Cl.
*A61B 1/04* (2006.01)
*H01R 24/38* (2011.01)
*A61B 1/045* (2006.01)
*A61B 1/00* (2006.01)
*H01R 13/66* (2006.01)

(52) U.S. Cl.
CPC ........... *A61B 1/045* (2013.01); *A61B 1/00124* (2013.01); *A61B 1/04* (2013.01); *A61B 1/042* (2013.01); *H01R 13/6683* (2013.01); *H01R 24/38* (2013.01)

(58) Field of Classification Search
CPC .............. A61B 1/042; A61B 1/00124; A61B 1/00121; H04R 24/38; H04R 39/06; H04R 13/6683
USPC ............................ 439/1, 11, 13, 20, 21, 290
See application file for complete search history.

(56) References Cited

U.S. PATENT DOCUMENTS

| | | | |
|---|---|---|---|
| 4,168,702 A * | 9/1979 | Ohshiro | A61B 1/04 396/17 |
| 4,611,888 A * | 9/1986 | Prenovitz et al. | A61B 1/042 348/75 |
| 4,797,737 A * | 1/1989 | Yazawa | A61B 1/042 348/73 |
| 5,378,549 A | 1/1995 | Eylon | |
| 5,469,403 A | 11/1995 | Young et al. | |
| 5,818,130 A | 10/1998 | Gass et al. | |
| 6,348,862 B1 | 2/2002 | McDonnell et al. | |
| 6,528,746 B2 * | 3/2003 | DeWitt | H01R 13/7037 200/51.09 |
| 6,690,159 B2 | 2/2004 | Burreson et al. | |
| 6,850,136 B2 | 2/2005 | McCollum et al. | |
| 6,894,509 B2 | 5/2005 | Johnson et al. | |
| 7,112,962 B2 | 9/2006 | Ricks et al. | |
| 7,239,108 B2 | 7/2007 | Best | |
| 7,310,286 B1 | 12/2007 | Jarvis et al. | |

(Continued)

FOREIGN PATENT DOCUMENTS

WO    WO 2009/151535 A1    12/2009

*Primary Examiner* — John P Luebecker
(74) *Attorney, Agent, or Firm* — Flynn, Thiel, Boutell & Tanis, P.C.

(57) ABSTRACT

At least two distinct electrical members each having electrical elements are provided. The electrical members are moveable with respect to each other and one or more sensors determine the relative position of the electrical members. The electrical members may be used in a medical device such as an endoscopic system.

24 Claims, 6 Drawing Sheets

(56) References Cited

U.S. PATENT DOCUMENTS

| | | | |
|---|---|---|---|
| 7,345,433 B2 | 3/2008 | Bacon et al. | |
| 7,408,343 B2 | 8/2008 | Dmytriw et al. | |
| 7,525,398 B2 | 4/2009 | Nishimura et al. | |
| 7,602,134 B1 * | 10/2009 | Taylor | F16M 11/08 310/232 |
| 7,701,203 B2 | 4/2010 | Fouts et al. | |
| 8,026,715 B2 | 9/2011 | Pozidis et al. | |
| 8,188,754 B2 | 5/2012 | Teterwak et al. | |
| 8,305,092 B2 | 11/2012 | Tabaczynski | |
| 8,672,228 B1 * | 3/2014 | Saini | H01R 11/30 235/486 |
| 2003/0009084 A1 * | 1/2003 | May | A61B 1/00188 600/112 |
| 2004/0147809 A1 * | 7/2004 | Kazakevich | A61B 1/0607 600/178 |
| 2007/0072442 A1 * | 3/2007 | DiFonzo | H01R 13/641 439/39 |
| 2008/0139881 A1 * | 6/2008 | Cover | A61B 1/00016 600/103 |
| 2009/0047824 A1 * | 2/2009 | Seibert | H01R 13/641 439/490 |
| 2010/0022829 A1 * | 1/2010 | Irion | A61B 1/00117 600/109 |
| 2010/0097051 A1 | 4/2010 | Bussan | |
| 2010/0201351 A1 | 8/2010 | Clymer | |
| 2010/0331734 A1 | 12/2010 | Stein | |
| 2011/0193949 A1 | 8/2011 | Nambakam et al. | |
| 2013/0181661 A1 * | 7/2013 | Workman | H02J 7/0042 320/107 |
| 2014/0213118 A1 * | 7/2014 | Glynn | A61N 1/3752 439/675 |
| 2015/0157196 A1 * | 6/2015 | Van Der Mark | A61B 1/00114 134/104.1 |

* cited by examiner

POWER SUPPLY THROUGH A SINGLE TRACK OF DISCRETE ELECTRODES AND METHOD THEREFOR

CROSS REFERENCE TO RELATED APPLICATION

This application claims the benefit of U.S. Provisional Application Ser. No. 61/782,632, filed Mar. 14, 2013, which is incorporated herein by reference in its entirety.

BACKGROUND OF THE INVENTION

The present invention generally relates to a power supply through a single track of discrete electrodes, and more specifically to a medical instrument that comprises a power supply through a single track of discrete electrodes.

Many medical instruments, including some handheld instruments, are not powered, often in the instance where one portion of the instrument moves with respect to another portion of the instrument. This results in a "passive" device, or a passive portion of a device, that is, one that does not receive electrical energy or signals. This is true of some instruments used in endoscopy.

Endoscopy in the medical field allows internal features of the body of a patient to be viewed without the use of traditional, fully invasive surgery. Endoscopic imaging systems incorporate endoscopes to enable a user to view a surgical site, and endoscopic tools enable noninvasive surgery at the site. The endoscope is placed in the body at the location at which it is necessary to perform the surgical procedure. Other surgical instruments are also placed in the body at the surgical site. A surgeon views the surgical site through the endoscope in order to manipulate the instruments to perform the desired surgical procedure. The endoscopes may be used with a camera head for the purpose of processing the image data received by the endoscope.

Currently, endoscopes are passive devices that provide an illumination channel and a viewing channel. The endoscopes have a proximal eyepiece which is inserted into an optical coupler, which in turn is connected to the camera head. Alternatively, the endoscope may contain the optical coupling pieces internally and interface directly with the camera head. The interface between the endoscope and the coupler or camera head is mechanical in nature due to requirements of sterilization, stability, reliability, and rotation of the endoscope relative to the camera head. Moreover, the endoscope must be autoclavable, meaning that the design must be robust enough to accommodate high temperatures and high pressures encountered during a sterilization cycle. These requirements have resulted in the endoscope being a passive device. Electrically active instruments such as endoscopes would garner many advantages. However, due to the above-noted structural features, to date the commercially available endoscopes have not been made electrically active.

Another factor in designing an endoscopic system is that the endoscope and camera head connection is made and broken at least once per medical procedure, which leads to a large number of connections being made and broken over the lifetime of the endoscopic system. Therefore, an endoscope with both electrical and mechanical connections is preferably at least as reliable as the current mechanical-only arrangement. While keeping all of these factors in mind, the endoscopic arrangement must also be easily manipulated by the user and remain compact, with the endoscope being free to rotate with respect to the coupler or camera head.

The embodiments of the present invention address and solve these problems. In one embodiment, a medical device system has a first member and a second member, the first member including a plurality of electrical elements, and the second member including a plurality of electrical elements and a plurality of proximity sensors. The proximity sensors are preferably magnetic in nature. The distinct electrical elements of the second member are connected to a dynamically switchable electrical circuit, the circuit including the proximity sensors. Such a structure results in the members' electrical polarity capable of being dynamically switched based on the relative position of the opposing electrical elements of the respective members. This provides discrete electrical contact throughout 360° of rotation of one member relative to the other, regardless of orientation and initial configuration. The medical device system may be an endoscope and camera head arrangement.

This system permits a hermetic seal to be achieved and allows rotation of the members with respect to one another. The method of sensing proximity and position may employ the use of Hall Effect sensors, magneto-resistive sensors, through-load detection, capacitive sensing devices, or other proximity/positioning sensing devices or apparatus.

Other advantages, objects and/or purposes of the invention will be apparent to persons familiar with constructions of this general type upon reading the following specification and inspecting the accompanying drawings.

DETAILED DESCRIPTION

Certain terminology will be used in this description for convenience and reference only, and will not be limiting. For example, the words "upwardly," "downwardly," "rightwardly," and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction toward the end of the arrangement which is furthest from the patient. This terminology will include the words specifically mentioned, derivatives thereof, and words of similar import.

Figure 1:
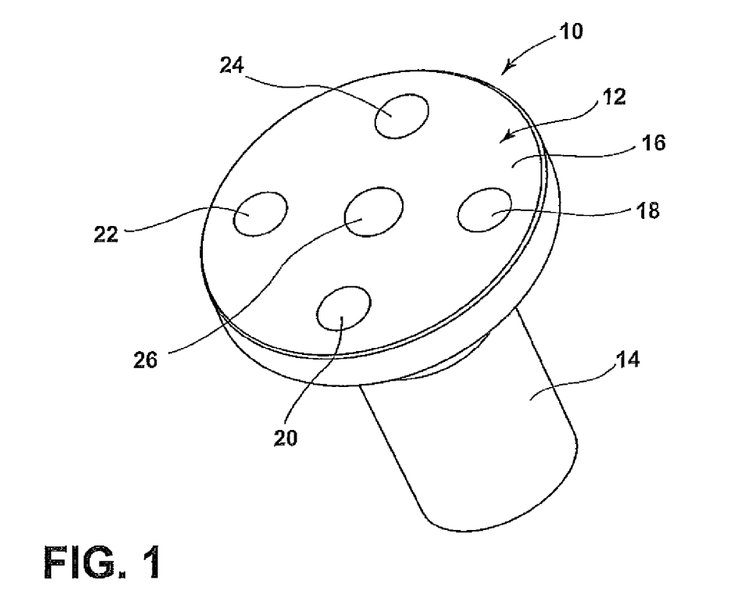
FIG. 1 is a perspective view of a first embodiment of a first electrical connection member having a plurality of electrical elements.

In FIG. 1, a first embodiment of a first electrical connection member 10 is depicted. The electrical connection member 10 includes a body 12 at one end and a coupling 14 attached to the body 12 for attachment to or engagement with another member or instrument. The body 12 is depicted as being circular, which is preferable, but it is contemplated that other shapes could be used as long as the body 12 is rotatable with respect to a second electrical connection member. The body 12 has a substantially flat end surface 16. The electrical connection member 10 also includes a central bore 26, to allow transmission of light therethrough or to receive mechanical components therein, if desired. Embedded in the body 12 are four electrical or signal elements 18, 20, 22, 24, the ends of which are substantially flush with the end surface 16 of the body 12. The elements 18, 20, 22, 24 are preferably equally spaced from one another. In one embodiment, two of the elements, such as 18 and 22, are electrical elements, and the other two elements 20, 24 are signal elements. Other variations are contemplated, and varying numbers of electrical elements and signal elements, including those disclosed herein elsewhere, are contemplated.

The electrical elements are adapted to transmit and/or receive electricity from a mate element in a second electrical connection member. The signal elements are for transmitting to, and/or receiving from, electrical signals of a mate element which may be used in operating or maintaining the device in which the electrical connection member is used.

Figure 2:
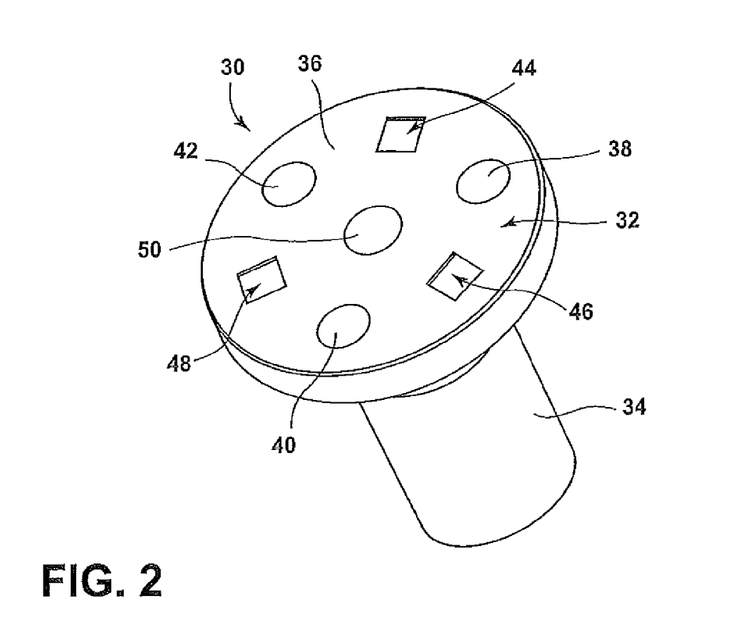
FIG. 2 is a perspective view of a second embodiment of a first electrical connection member having a plurality of electrical elements and positioning elements.

FIG. 2 depicts a second embodiment of a first electrical connection member 30. The electrical connection member 30 includes a body 32 at one end and a coupling 34 attached to the body 32 for attachment to an instrument or a part of an instrument. The body 32 has a substantially flat end surface 36, and, as shown in FIG. 2, three electrical or signal elements 38, 40, 42. The electrical or signal elements 38, 40, 42 are preferably equally spaced from each other at the surface 36 of the body 32. The body 32 is preferably circular in shape but may be other shapes. The ends of the elements 38, 40, 42 are substantially flush with the end surface 36 of the body 32. The electrical connection member 30 also includes three proximity elements 44, 46, 48, which are preferably spaced equally about the body 32, and are preferably comprised of a metallic substance. Each proximity element is spaced centrally between two electrical or signal elements. The proximity elements 44, 46, 48 each extend to a position that is adjacent the end surface 36 of the body 32, and may be in the form of magnets, coils, or metallic elements. The electrical connection member 30 also includes a central elongated bore 50 which extends at least through the body 32 and into the coupling 34. The central elongated bore 50 may be used to allow light to pass therethrough or to receive mechanicam components therein.

Figure 3:
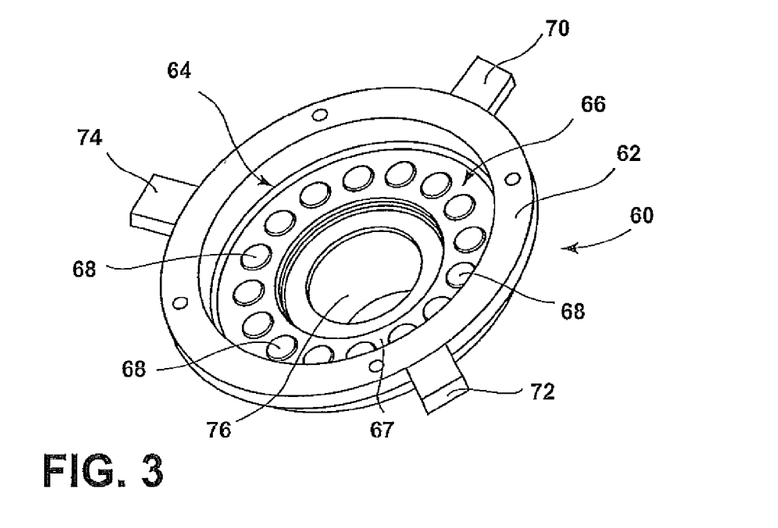
FIG. 3 is a perspective view of a first embodiment of a second electrical connection member having a plurality of electrical elements and a plurality of sensors.

FIG. 3 shows a first embodiment of a second electrical connection member 60, that is, an electrical connection member which may mate with an electrical connection member such as the first electrical connection member 10 or the first electrical connection member 30. The electrical connection member 60 includes a base 62 which is preferably circular in shape and substantially cylindrical in nature, and defines a central space 64 therein. The space 64 is sized and shaped to receive at least a portion of a body of a first electrical connection member such that the second electrical connection member 60 may engage with a first electrical connection member in a rotatable fashion. The base 62, and the inner space 64, terminate in an inner wall 66 which has an external surface 67. The wall 66 has embedded therein or attached thereto a plurality of electrical contact members 68. In FIG. 3, the electrical contact members 68 are shown as metal pins, the ends of which are exposed and are adjacent the surface 67 of the wall 66. The electrical contact members 68 may be in a different form than a metal pin and more or less than the 16 depicted in FIG. 3 may be employed. A plurality of sensors are attached to the base 62. The sensors 70, 72, 74 are preferably equally spaced about the periphery of the outer base 62 and are designed to sense proximity and position of relative electrical or signal elements. The sensors 70, 72, 74 may be any kind of sensors capable of sensing position and proximity of electrical elements, such as Hall Effect sensors, magneto-resistive sensors, load detection sensors or capacitive sensors. The second electrical connection member 60 also includes a central bore 76 to allow the passage of light therethrough or to receive other components therein.

Figure 4:
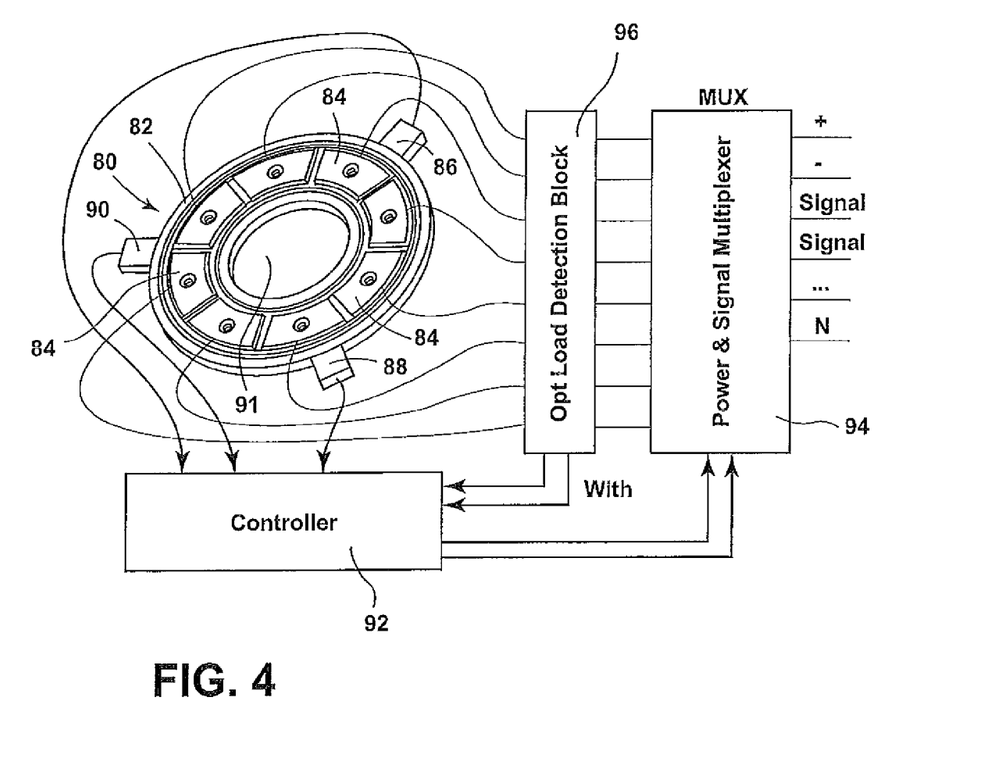
FIG. 4 is a perspective view of a second embodiment of a second electrical connection member having a plurality of electrical elements and a plurality of proximity sensors, and associated electronic components.

A second embodiment of a second electrical connection member 80 is depicted in FIG. 4. The second electrical connection member 80 includes a base 82 which is preferably circular in shape. The base 82 has attached thereto a plurality of metallic pads 84, which in combination create an array of electrical contacts. Eight electrical metallic pads are depicted in FIG. 4, but more or less may be employed. The metallic electrical pads 84 are for the purpose of transmitting and/or receiving electrical energy or signals to or from a first electrical connection member such as electrical connection member 10 or electrical connection member 30. The second electrical connection member 80 also includes a plurality of proximity and position sensors. The proximity and position sensors 86, 88, 90 are located at the periphery of the base 82 of the second electrical connection member 80. The sensors are preferably spaced equally about the base 82 and more or less sensors may be employed. However, if elements such as metallic elements 44, 46, 48 of the first electrical connection member 30 are used, it is preferable that the second electrical connection member have the same number of proximity and position sensors as metallic elements of the first electrical connection member. The sensors 86, 88, 90 are in communication with a controller 92, which in turn provides signals to a power and signal multiplexer 94. The electrical pads 84 are connected to an optimum load detection block 96, which is in turn connected to the multiplexer 94. In addition, the detection block 96 communicates with the controller 92 so that electricity or signals are supplied to the correct electrical pads 84 based on the relative position of the second electrical connection member 80 to a first electrical connection member.

Figure 5:
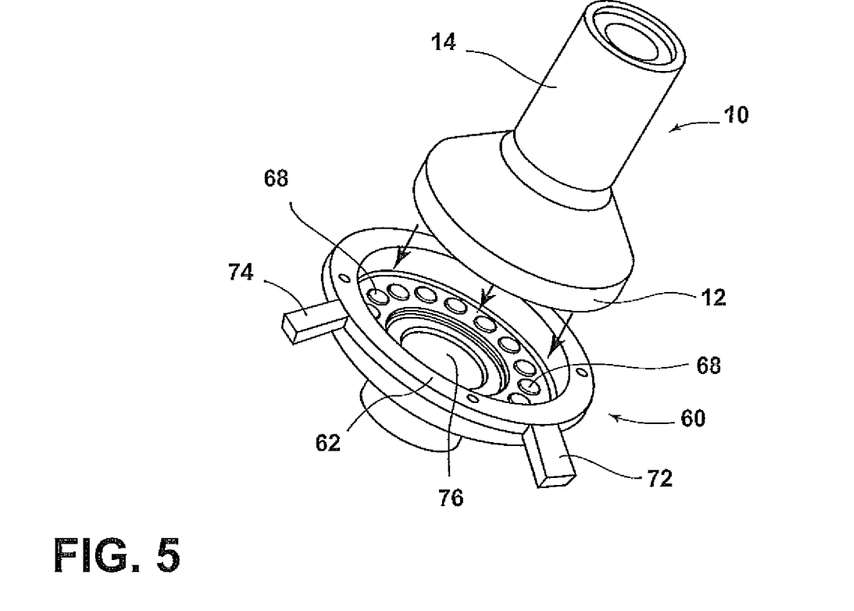
FIG. 5 is a perspective view of the first electric connection member of FIG. 1 and the second electrical connection member of FIG. 3, depicting their relative position prior to connection.

FIG. 5 shows the arrangement of the first electrical connection member 10 and the second electrical connection member 60 prior to engagement. The first electrical connection member 10 is aligned with the second electrical connection member 60 as shown in FIG. 5. The first electrical connection member 10 is then moved in the direction of the arrows in FIG. 5 to engage the first electrical connection member 10 with the second electrical connection member 60. The two electrical connection members are preferably attached in a sealable fashion, in such a way that is known in the industry. After attachment, the first electrical connection member 10 remains rotatable with respect to the second electrical connection member 60.

Figure 6:
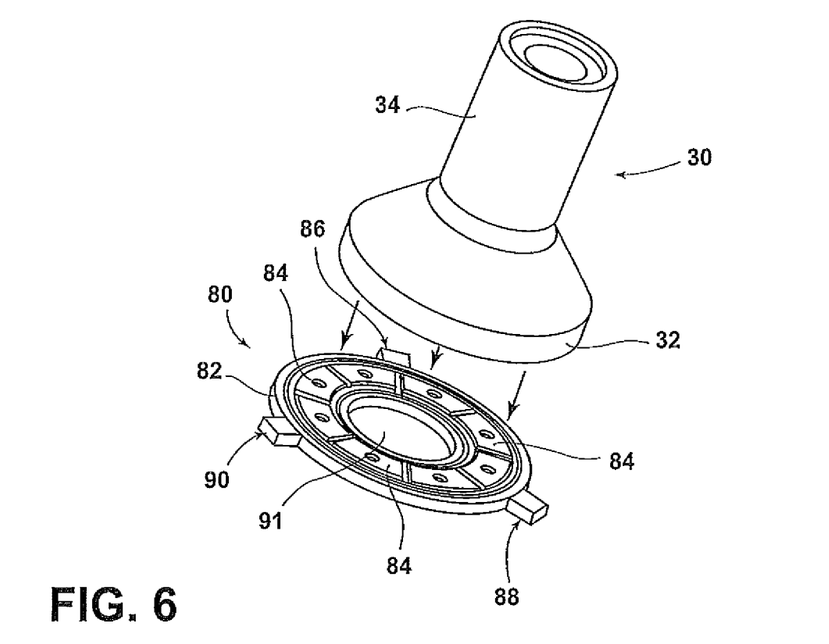
FIG. 6 is a perspective view of the first electrical connection member of FIG. 2 and the second electrical connection member of FIG. 4, depicting their relative position prior to connection.

In FIG. 6 the arrangement of the first electrical connection member 30 with respect to the second electrical connection member 80 prior to engagement is shown. The first electrical connection member 30 is aligned with the second electrical connection member 80 as shown in FIG. 6. The first electrical connection member 30 is then moved in the direction of the arrows in FIG. 6 to engage the first electrical connection member 30 with the second electrical connection member 80. The respective electrical connection members are preferably attached in a sealable, but rotatable fashion such that the first electrical connection member 30 may be rotated with respect to the second electrical connection member 80.

Figure 7:
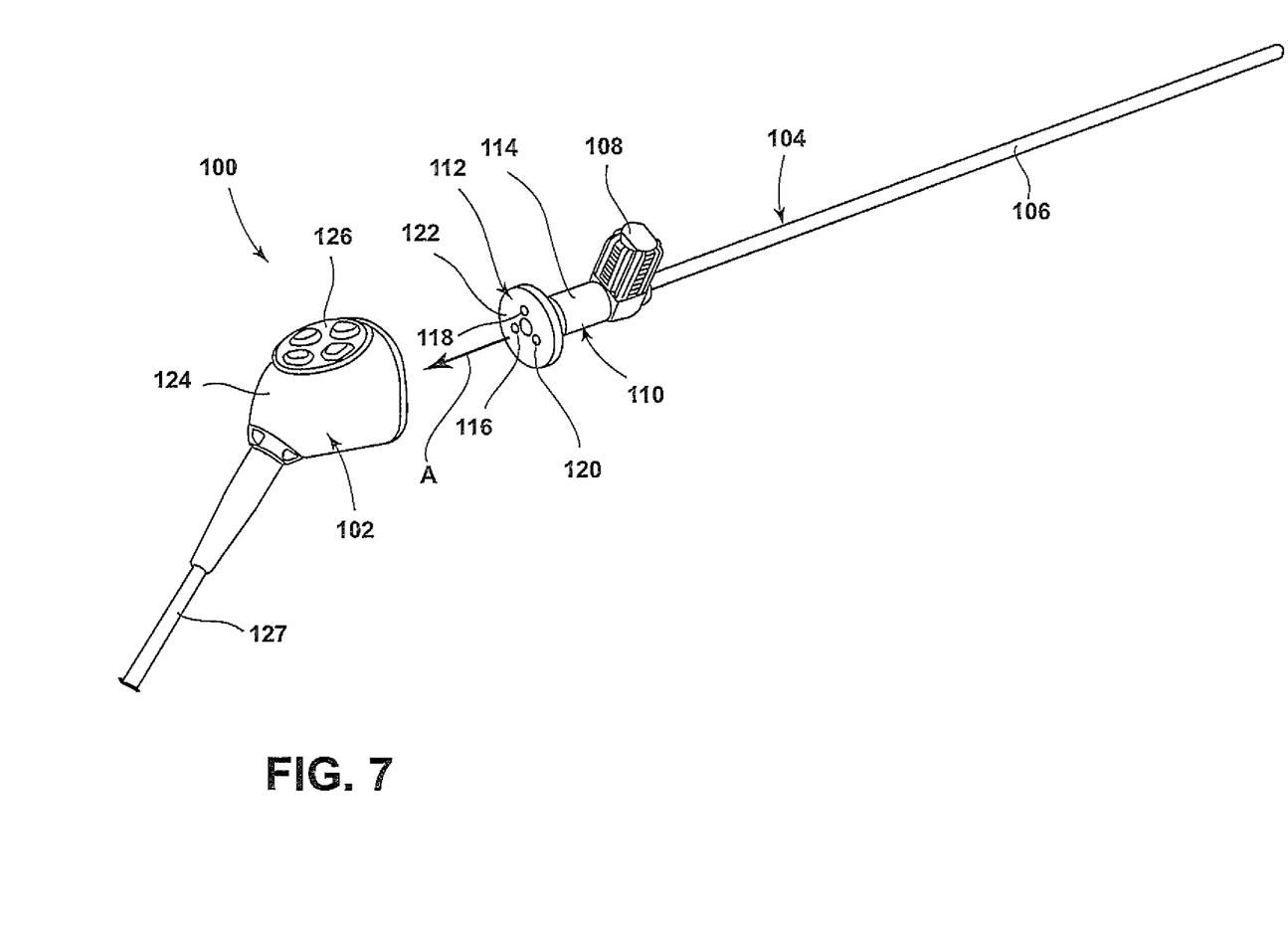
FIG. 7 is a perspective view of an endoscope with an integrated LED and a first electrical connection member, and an adjacent camera head which is movable relative to the endoscope and which has a second electrical connection member.
Figure 8:
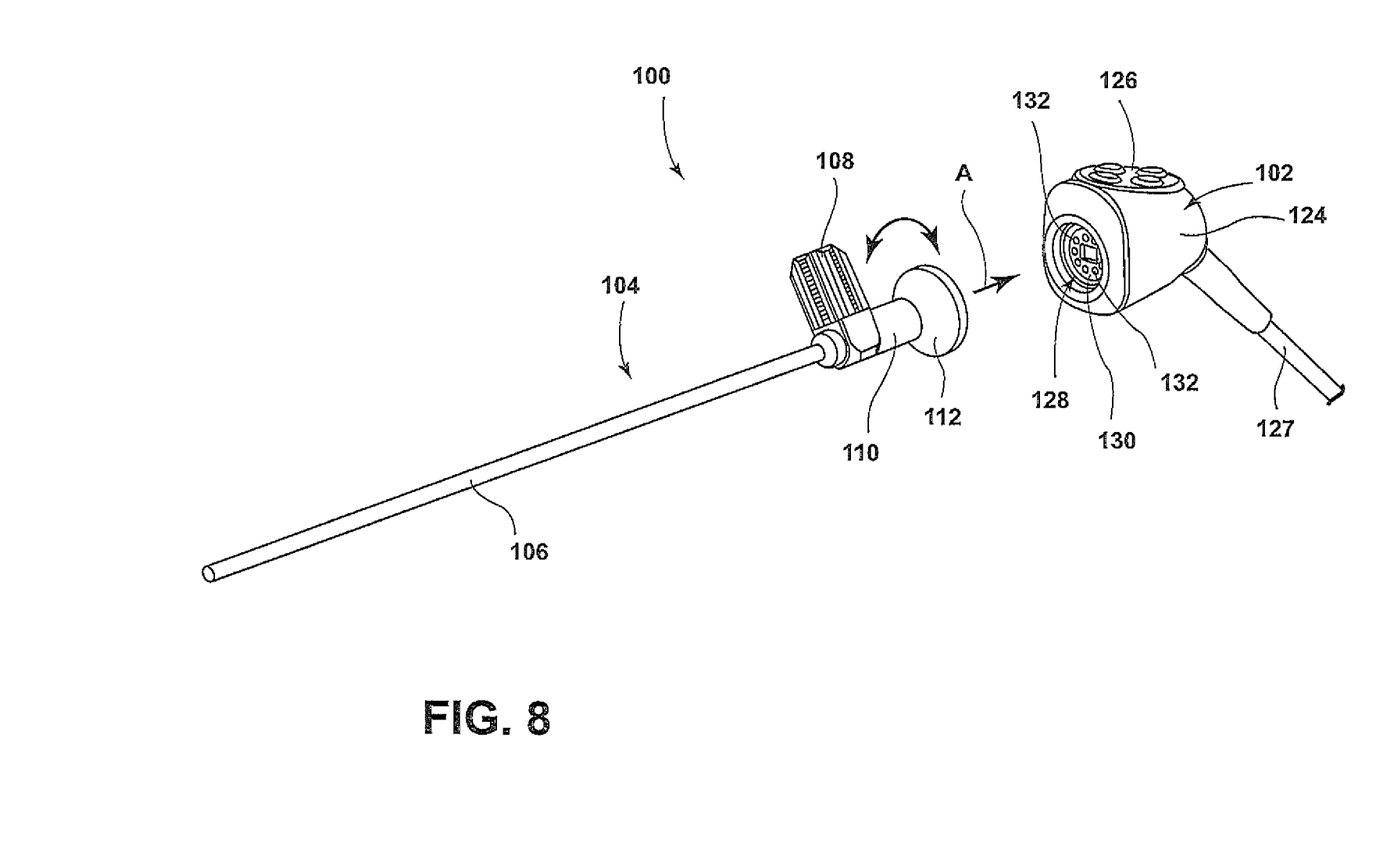
FIG. 8 is a perspective view of the endoscope and camera head of FIG. 7, depicted from the opposite direction as FIG. 7.

FIGS. 7-8 show an example of an instrument in which the electrical connection members depicted in FIGS. 1-4 may be used. The instrument depicted in FIGS. 7-8 is an endoscopic system 100 which has two main components as shown, a camera head 102 and an endoscope 104. The endoscope 104 includes an elongated tube 106 through which light may pass from a light source to a surgical site, and through which light may pass from a surgical site to the camera head 102. The endoscope 104 further includes an integrated LED light source 108 which is capable of providing light to and through the endoscope tube 106 to a surgical site. The endoscope 104 also includes a first electrical connection member 110 at the proximal end of the endoscope 104. The first electrical connection member 110 includes a body 112 and a coupling 114. The coupling 114 is used for attachment of the first electrical connection member 110 to the remainder of the endoscope 104. As shown in FIG. 7, the body 112 has three electrical/signal elements 116, 118, 120 embedded therein, the ends of which are adjacent an outer surface 122 of the body 112. Preferably, two of the elements are electrical elements and the third is a signal element. However, the number of electrical elements and signal elements may vary, depending on the specific instrument and application of use. The body 112 of the member 110 includes a central bore 123 which allows light from the endoscope tube 106 to pass therethrough.

Figure 9:
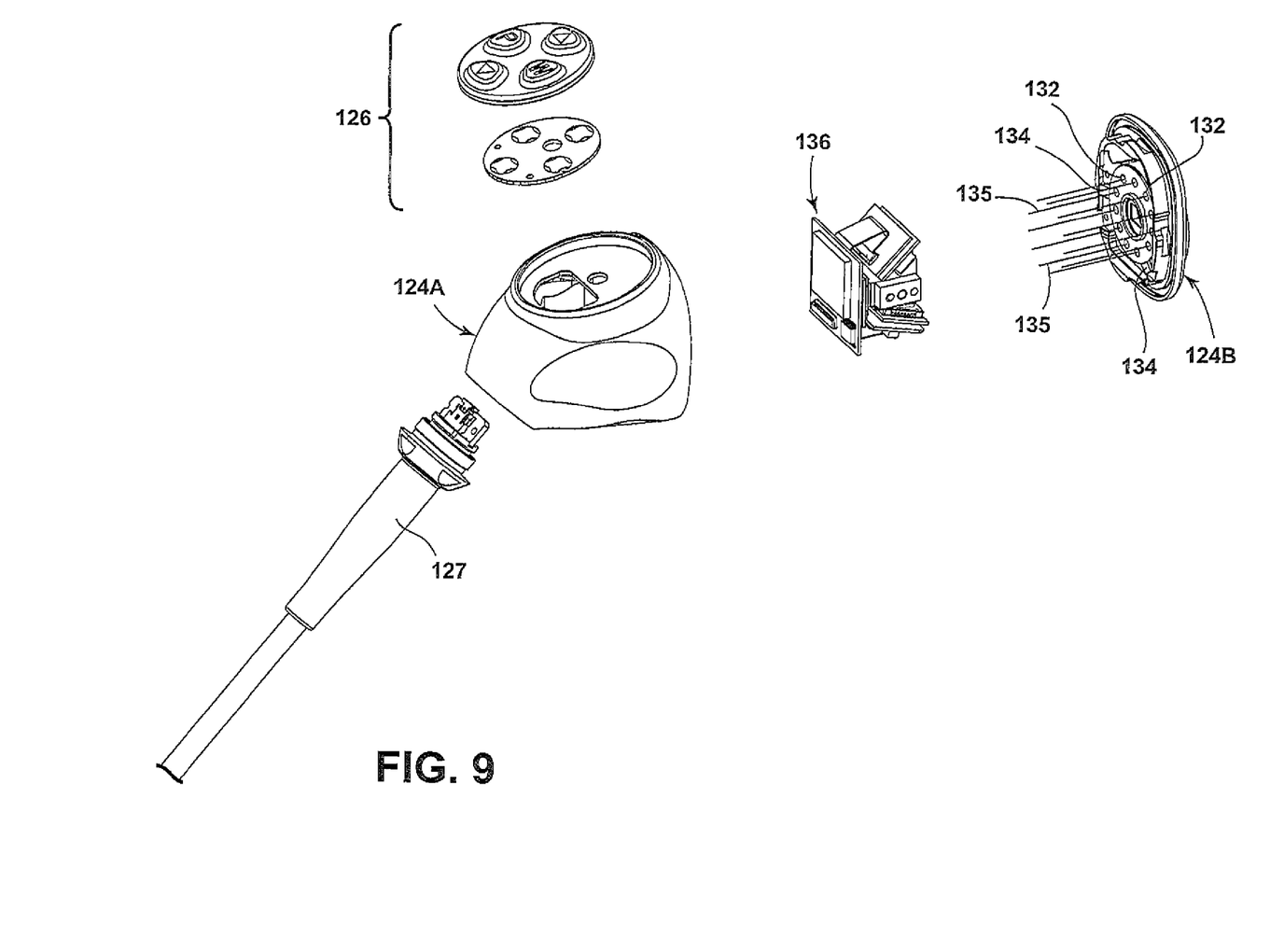
FIG. 9 is an exploded perspective view of the camera head of FIGS. 8-9.

The camera head 102 includes a housing 124 to which is attached a control pad 126 and which includes an internally disposed camera unit 136 (see FIG. 9). The housing 124 includes a rear enclosure part 124A and a front enclosure part 124B (see FIG. 9). The camera head 102 is connected to a transmission cable 127, which is in turn connected to an electronic component such as a camera control unit (CCU). At its distal end, the camera head 102 includes a connection port 128 (see FIG. 8). The connection port 128 is configured to receive a coupler or another instrument in a sealable and rotatable arrangement. Adjacent to, or creating a part of, the connection port 128 is a second electrical connection member 130. The second electrical connection member 130 includes a plurality of electrical contact members 132 such as pins, as well as sensors 134. The pins 132 receive and transmit electrical energy and/or signals. The pins 132 have elongated portions 135, which extend through the housing 124 of the camera head 102, as shown in FIG. 9.

The endoscope 104 and the camera head 102 are connected by moving the endoscope 104 in the direction of the arrow A in FIGS. 7-8 toward the camera head 102, moving the body 112 of the first connection member 110 into the port 128 of the camera head 102. The endoscope 104 is rotatably and sealably attached to the camera head 102, and the first electrical connection member 110 is engaged with the second electrical connection member 130. Powering of the device 100, through the camera head 102, results in power being supplied through the second electrical connection member 130 via the electrical contact members 132 to one or more of the electrical/signal elements 116, 118, 120 of the first electrical connection member 110 of the endoscope 104. This results in electrical power and/or electrical signals being supplied to the first electrical connection member 110 and thus to the endoscope 104. Using such an arrangement, the integrated LED 108 may be powered to provide light to the endoscope. Likewise, signals from the LED or another electrical component may be supplied through the first electrical connection member 110 to the second electrical connection member 130 via one or more of the elements 116, 118, 120 to one or more of the electrical contact members 132. The electricity and/or signals can then be transmitted through the transmission cable 127 to another component of the system, such as a detection block. Upon rotation of the endoscope 104 with respect to the camera head 102, sensors 134 of the second electrical connection member 130 sense the proximity and position of the electrical signal elements 116, 118, 120 with respect to the various electrical contact members 132 such that the electricity and signals are provided to the correct elements in both directions.

This arrangement results in a system, such as an endoscopic system, in which electrical energy and/or signals may be transferred from a first device to a second device, where the first device is rotatable with respect to the second device. Such a system has the advantage of eliminating one or more electrical stand-alone components which typically would have to be connected (either hard-wired or wirelessly) to the second device. Thus, when using the present invention, the second device becomes active electrically instead of passive.

We claim:

1. An apparatus comprising:
 a medical device including:
  a first part having a first electrical connection member, the first electrical connection member having a first member body with a surface and a plurality of first elements for electrical or signal reception or transmission, the first elements each having an end adjacent the first member body surface; and
  a second part having a second electrical connection member, the second electrical connection member having a second member body with a surface and a plurality of second elements for electrical or signal reception or transmission, the second elements each having an end adjacent the second member body surface, the second electrical connection member further comprising a plurality of proximity sensors,
  the first part and the second part rotatably engaged with each other, the proximity sensors configured to sense the relative circumferential positions of the first elements and the second elements.

2. The apparatus of claim 1, wherein the medical device is an endoscopic system.

3. The apparatus of claim 2, wherein the first part is an endoscope and the second part is a camera head.

4. The apparatus of claim 1, wherein the first electrical connection member further includes metal proximity elements.

5. The apparatus of claim 1, wherein the surface of the first member body is substantially flat and each of the plurality of first elements have an end adjacent the surface of the first member body.

6. The apparatus of claim 1, wherein the second elements are pins.

7. The apparatus of claim 1, wherein the second elements are plates.

8. The apparatus of claim 1, wherein the second elements provide signals to a load detection block.

9. The apparatus of claim 1, wherein the sensors are Hall Effect sensors.

10. The apparatus of claim 1, wherein the sensors are magneto-resistive sensors.

11. The apparatus of claim 1, wherein the sensors are load detection sensors.

12. The apparatus of claim 1, wherein the sensors are capacitive sensing sensors.

13. The apparatus of claim 1, the proximity sensors receive and provide information to ensure that electricity and signals are provided correctly to both the first elements and the second elements.

14. An endoscopic system comprising:
   an endoscope having a tube, an electrically powered device, and a first electrical connection member, the first electrical connection member having a first member body with a surface and a plurality of first elements for electrical or signal reception or transmission, the first elements each having an end adjacent the first member body surface; and
   a camera head having a second electrical connection member, the second electrical connection member having a second member body with a surface and a plurality of second elements for electrical or signal reception or transmission, the second elements each having an end adjacent the second member body surface, the second electrical connection member further comprising a plurality of proximity sensors capable of sensing the relative circumferential position and proximity of the first elements and the second elements upon rotation of the first member body with respect to the second member body,
   the endoscope and the camera head rotatably engaged with each other such that the electrically powered device receives electricity from the camera head even when the endoscope is rotated relative to the camera head.

15. The endoscopic system of claim 14, wherein the second elements are pins.

16. The endoscopic system of claim 15, wherein the camera head has a housing and the pins extend into the camera head housing.

17. The endoscopic system of claim 14, wherein the electrically powered device is a light source.

18. The endoscopic system of claim 17, wherein the light source comprises an LED.

19. The endoscopic system of claim 14, wherein the electrically powered device is electrically powered entirely by electricity provided through the second electrical connection member.

20. The endoscopic system of claim 14, wherein the endoscope and camera head are attached to one another in a sealed fashion.

21. A method of supplying signals and electrical power through a single track of discrete electrical contacts, the method comprising:
   providing a first part having a first electrical connection member, the first electrical connection member having a first member body with a surface and a plurality of first elements for electrical or signal receipt or transmission, the first elements each having an end adjacent the first member body surface;
   providing a second part having a second electrical connection member, the second electrical connection member having a second member body with a surface and a plurality of second elements for electrical or signal receipt or transmission, the second elements each having an end adjacent the second member body surface, the second electrical connection member further comprising a plurality of proximity sensors capable of sensing the relative position and proximity of the first elements and the second elements, the first part and the second part rotatably engaged with each other; and
   the sensors sensing circumferential proximity and position of the first elements with respect to the second elements and assimilating the circumferential proximity and position of the first elements to ensure each electrical or signal receipt or transmission is provided correctly to the first elements and the second elements.

22. The method of claim 21, wherein the sensors provide signals to a controller.

23. The method of claim 22, further comprising the step of providing a multiplexer in communication in the controller, the multiplexer capable of providing multiple signals and electricity to the second elements based on the relative position of the first part to the second part.

24. A method of supplying signals and electrical power through a single track of discrete electrical contacts, the method comprising:
   providing a first part having a first electrical connection member, the first electrical connection member having a first member body with a surface and a plurality of first elements for electrical or signal receipt or transmission, the first elements each having an end adjacent the first member body surface;
   providing a second part having a second electrical connection member, the second electrical connection member having a second member body with a surface and a plurality of second elements for electrical or signal receipt or transmission, the second elements each having an end adjacent the second member body surface, the second electrical connection member further comprising a plurality of proximity sensors capable of sensing the relative position and proximity of the first elements and the second elements, the first part and the second part rotatably engaged with each other;
   the sensors sensing proximity and position of the first elements; and
   the sensors providing signals to a controller; and
   providing a multiplexer in communication in the controller, the multiplexer capable of providing multiple signals and electricity to the second elements based on the relative position of the first part to the second part.

* * * * *